United States Patent
Kuris et al.

(10) Patent No.: US 8,441,371 B2
(45) Date of Patent: *May 14, 2013

(54) METHOD AND MECHANISM FOR ASSISTED DIAGNOSIS AND MAINTENANCE OF HEALTH MONITORING SYSTEM

(75) Inventors: Benjamin Kuris, Brookline, MA (US); Donald R. Denning, Jr., Shirley, AA (US); Steven M. Ayer, Marblehead, MA (US)

(73) Assignee: Intel-GE Care Innovations LLC, Roseville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/618,584

(22) Filed: Sep. 14, 2012

(65) Prior Publication Data
US 2013/0009772 A1    Jan. 10, 2013

Related U.S. Application Data

(63) Continuation of application No. 11/646,599, filed on Dec. 28, 2006.

(51) Int. Cl.
  G08C 19/16   (2006.01)
  C08B 1/08    (2006.01)

(52) U.S. Cl.
  USPC .................................. 340/870.01; 340/539.22

(58) Field of Classification Search .......................... None
See application file for complete search history.

(56) References Cited

U.S. PATENT DOCUMENTS

| | | | |
|---|---|---|---|
| 5,640,143 A | 6/1997 | Myron et al. | |
| 6,351,713 B1 | 2/2002 | Board et al. | |
| 7,142,123 B1 | 11/2006 | Kates | |
| 7,399,277 B2 | 7/2008 | Saidara et al. | |
| 2001/0028308 A1 | 10/2001 | De La Huerga | |
| 2002/0158775 A1 | 10/2002 | Wallace | |
| 2003/0093719 A1 | 5/2003 | Ali-Santosa et al. | |
| 2003/0128118 A1 | 7/2003 | Leyden et al. | |
| 2004/0139048 A1 | 7/2004 | Kerr et al. | |
| 2005/0017873 A1 | 1/2005 | Liu et al. | |
| 2006/0028335 A1 | 2/2006 | Glenn et al. | |
| 2006/0062201 A1 | 3/2006 | Funk et al. | |
| 2006/0155818 A1 | 7/2006 | Odenwald et al. | |
| 2006/0190458 A1 | 8/2006 | Mishina et al. | |
| 2006/0242285 A1 | 10/2006 | Moriwaki | |
| 2007/0069892 A1 | 3/2007 | Paul et al. | |
| 2008/0157959 A1 | 7/2008 | Kuris et al. | |

FOREIGN PATENT DOCUMENTS

KR    1020040031733    4/2004

OTHER PUBLICATIONS

International Preliminary Report on Patentability issued on Jun. 30, 2009 in International Application No. PCT/US2007/089055.
Chinese Office Action with English language translation corresponding to International Application CN 200710305273.7, dated Aug. 27, 2010.

*Primary Examiner* — Brian Zimmerman
*Assistant Examiner* — Cal Eustaquio
(74) *Attorney, Agent, or Firm* — Pillsbury Winthrop Shaw Pittman LLP

(57) ABSTRACT

The invention relates to a system and method of a health monitoring network which automates detection of faulty or failed sensors using realt-time fault checking on a dynamically registered sensor data stream. The monitoring system and sensor network can provide a one-touch system to notify users when a sensor requires attention, without prior knowledge of the operational characteristics, installation method or configuration of sensors in the network. The network uses a decision engine to assist in maintenance according to a profile based on individual preferences and capabilities.

14 Claims, 7 Drawing Sheets

Figure 1

Exemplary Psuedo-code for Decision Engine:
...
<IF> UserButton pressed
<THEN> *query* BatteryVoltage for all Sensors[n]
  <IF> Sensor[i] has CriticalBatteryLevel
  <THEN> *IndicateAttention* on Sensor[i]
    <ELSE> *Load* MaintenenceProfile
      <IF> Sensors match MaintenanceProfile
      <THEN> *SelectBestSensor* out of Sensors[m]
            *IndicateAttention* on Sensor[j]

Figure 2

Continuous Loop based on Sample Rate

METHOD AND MECHANISM FOR ASSISTED DIAGNOSIS AND MAINTENANCE OF HEALTH MONITORING SYSTEM

CROSS-REFERENCE TO RELATED APPLICATIONS

This application is related to and claims the benefit under 35 U.S.C. 120 of U.S. application Ser. No. 11/646,599, filed on Dec. 28, 2006, the entire contents of which is incorporated herein by reference.

FIELD OF THE INVENTION

The invention relates to a system and method of a health monitoring network which automates detection of faulty or failed sensors, assists in the maintenance of, the configuration of customizable profiles based on preferences and capabilities.

BACKGROUND

Existing solutions are designed with limited run time to avoid the need for unsupervised system maintenance. Administration requires expertise and training in the system. Additionally, work on multi-sensor health monitoring systems focuses on communication methods, data analysis, and transducer efficacy. Practical issues in on-body multi-sensor deployment such as maintaining a multi-sensor system with zero-training and minimal inconvenience is virtually nonexistent.

Common methods include some form of the BIST (built-in self test) on sensor nodes, and manual inspection of data during installation and after loss of data is detected. The execution or interpretation of results from these methods requires technical knowledge that most users lack. Finally, there are substantial periods of missing data when manual inspections are not regularly conducted.

DETAILED DESCRIPTION

The present invention relates to system design of a Health Monitoring sensor network that uses a decision engine to assist in maintenance according to a profile based on individual preferences and capabilities. The invention is applicable to maintenance of physical attributes of sensors that change over time. One embodiment is in the maintenance of a system of battery powered sensors.

In one embodiment of the invention, there is a system and method for maintaining a network. A base station provides a user the ability to invoke assistance in maintaining the network; at least one sensor to communicate status information to the base station; and a decision engine embedded in the base station to access the status information and activate sensor attention indicators based on a stored profile.

In one aspect of the invention, the base station bi-directionally communicates with the at least one sensor to determine the status information and verify signal quality based upon expected range and rate of change of the sensor reading.

In another aspect of the invention, a fault-detection service checks data of the at least one sensor, wherein the fault-detection service is located in the base station or on a remote computing resource.

In still another aspect of the invention, the user is notified of detected faults on one of the at least one sensors.

In yet another aspect of the invention, the base station hosts a secure, remotely-configurable bridge to the network.

In another aspect of the invention, the at least one sensor has a visual and/or audible alarm identifiable by the user.

In still another aspect of the invention, the at least one sensor is a MEMs accelerometer.

Figure 6:
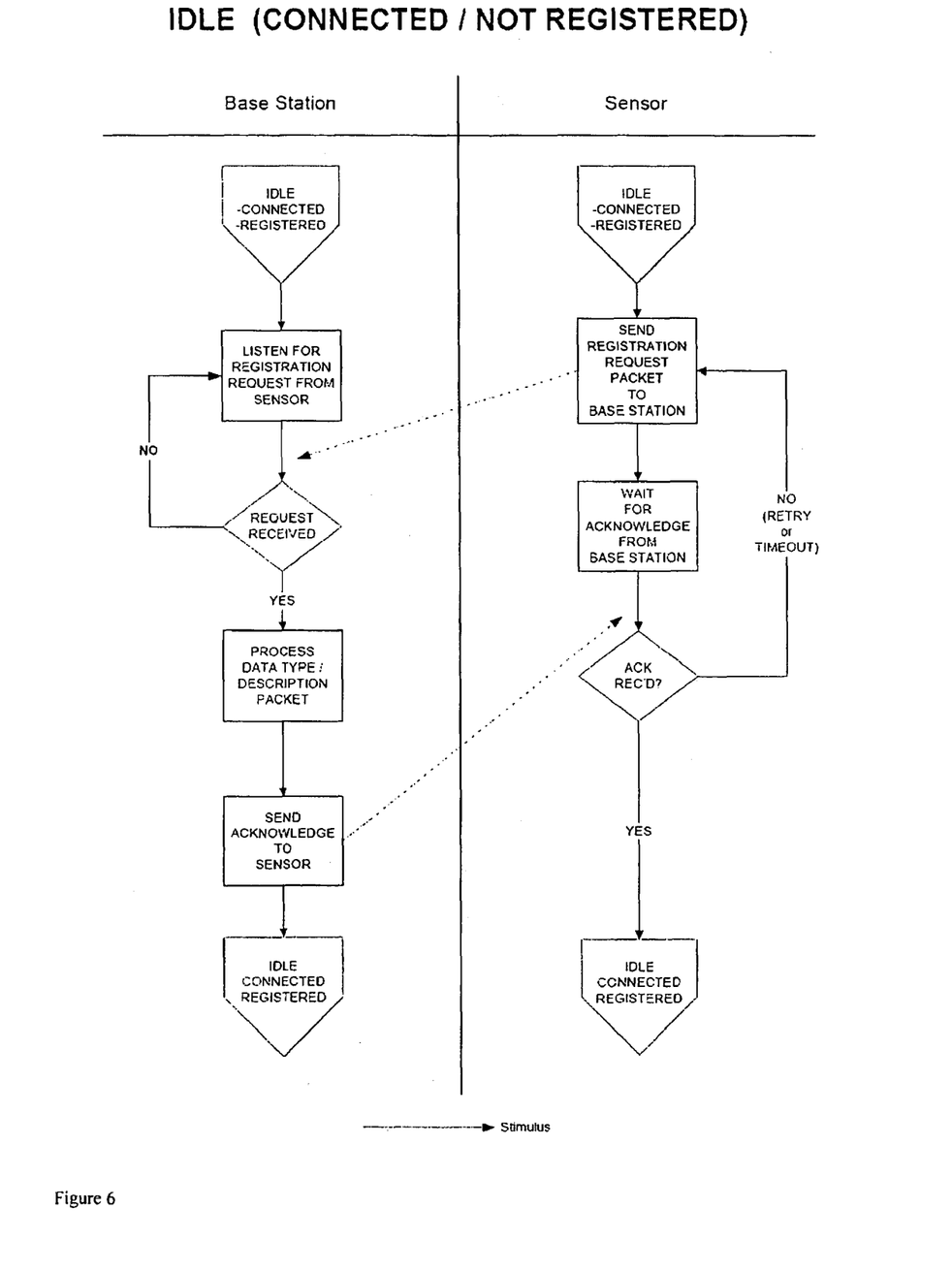
FIG. 6 illustrates an exemplary flow of data between the base station and sensor when the base station is connected and the sensor is not connected.

In yet another aspect of the invention, and upon initialization of communication between the base station and the at least one sensor, a registration process occurs (see FIG. 6).

In one aspect of the invention, the registration process comprises the at least one sensor sending header information to the base station including at one of the following: information about data-type for scalar quantity measure by the device, valid range, units for the scalar, frequency of delivery, and a descriptive character string; and the base station replies with an acknowledgement message (see FIG. 6).

Figure 7:
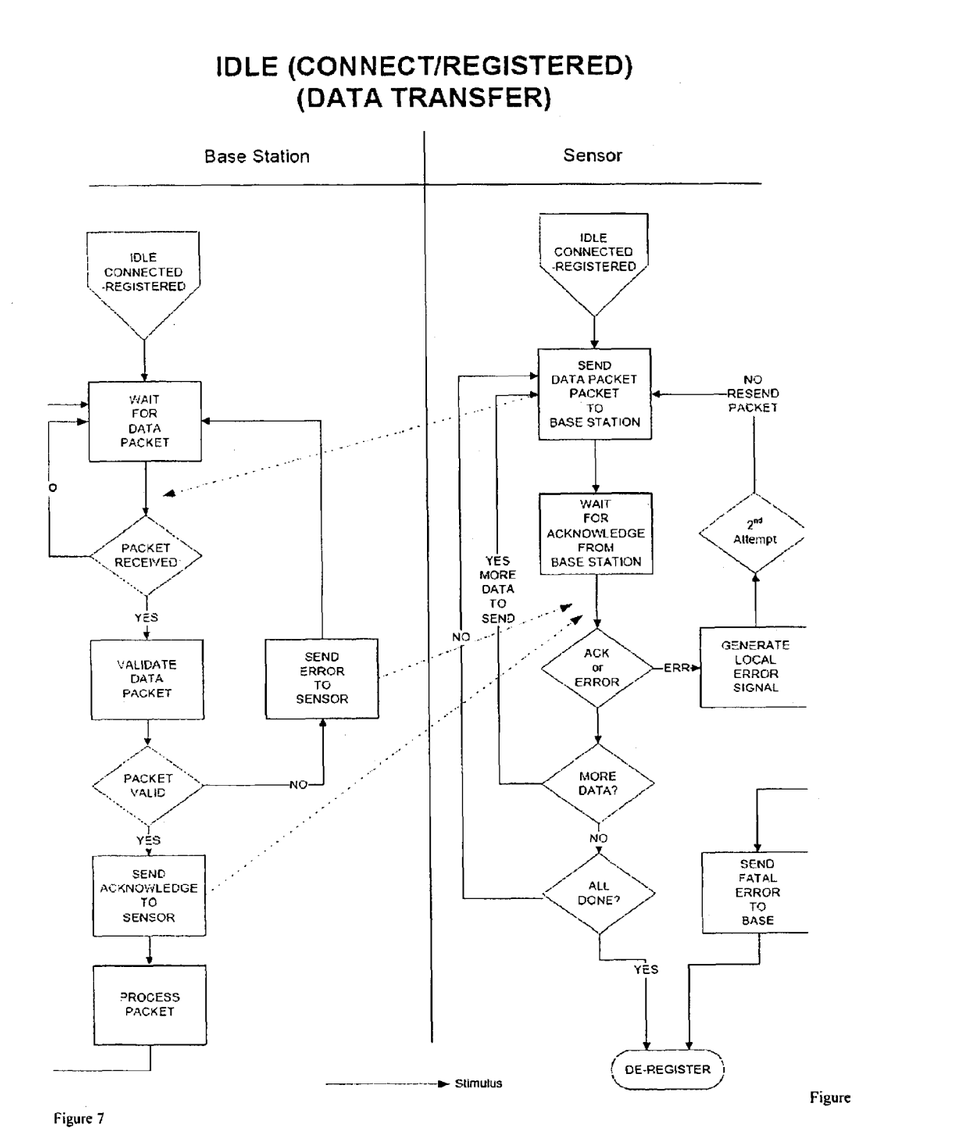
FIG. 7 illustrates an exemplary flow of data between the base station and sensor when both are connected and data transfer occurs.

In another aspect of the invention, and upon receipt of an error signal from the base station, the at least one sensor actuates a user detectable alarm (see FIG. 7).

In still another aspect of the invention, the decision engine is customizable and includes a user stored profile based on data supplied by a healthcare provider or patient sensing requirements.

Exemplary elements of the invention are:
A) Coordinating base-station with:
  1) Method for user to invoke assistance in maintaining a sensor network.
  2) Ability to communicate with sensors to determine status of consumables such as power and chemical agents and verify signal quality from affixed sensors that might "fall off" during activity.
  3) Physical interface to refresh depleted sensor resources.
B) Wearable sensors with:
  1) Ability to communicate status to coordinating base-station (as described above).
  2) Ability to attract user attention such as a blinking indicator or audible alarm.
C) Decision engine that can:
  1) Access sensor status information.
  2) Activate sensor attention indicators based on a stored profile.
  3) Be customized according to health care provider or patient preferences, capabilities of the sensor and the intended monitoring plan In another embodiment of the invention, there is a method to provide assistance in the maintenance of a health monitoring system by automating detection of faulty or failed sensors using real-time fault-checking on a dynamically registered sensor data stream. The monitoring system and sensor network can provide a one-touch system to notify users when a sensor requires attention. The user need not have prior knowledge of the operational characteristics, installation method, or configuration of sensors in the network to unambiguously detect a fault.

Additional exemplary elements are:

A base station that has the ability to conduct bi-directional communications with sensors in the health monitoring system. Data from each sensor is presented to a fault-detection service for checking and the results are used to notify users of faults on specific sensors at an opportune time. The base station hosts a secure, remotely-configurable bridge to the local health monitoring network.

A number of portable sensors that can, upon initialization, notify the base station of the nature of their data transmissions, and accept a message from the base station that triggers either a visible or audible trouble indicator.

A fault-detection service that can select and apply data-checking based on a library of methods associated with specific registered data types and available computational resources.

This invention addresses the problem(s) of:

Deploying and maintaining a long-term multi-sensor system offers new diagnostic and intervention options for a wide range of conditions. The adoption of these systems requires new methods of automated assistance because in many cases the target population has limited knowledge of technology, physical or cognitive impairment, and limited patience for sensing systems that further marginalize their quality of life.

The diminutive form-factor of on-body sensors in multi-sensor systems requires regular intervention to maintain effectiveness in long-term monitoring scenarios. In a multi-sensor system the complexity of maintenance is multiplied and will require new methods of user assistance and deployment.

Self-powered sensors located around users (environmental sensors) offer advantages for mass-casualty events and other temporary deployments. Minimizing maintenance overhead while ensuring reliable operation is a strong product advantage.

The invention provides a method of assisted maintenance based on system components that are well understood.

This invention simplifies the maintenance of a health monitoring sensor system by autonomously validating data from a dynamic group of homogeneous or heterogeneous sensors, and provides a facile method that requires no user training for locating a faulty sensor.

Examples of fault conditions include:
1) Sensors that are dislodged from their mounting point.
2) Sensors with consumable properties or limited operating lifetime.
3) Sensors that become inoperable due to power transients or corrupted memory.
4) Sensors that become inoperable due to tampering by visitors, pets or pests.

For long term sensing, the method and mechanism described will limit the burden on the patient according to a customizable profile that guides a decision engine. The system will assist the user in preventative maintenance of the sensor network at the user's request. This method is easily adapted into the patient's daily routine.

The direct result will be longer periods of multi-sensor data capture on a wider range of individuals.

The consumable aspects of sensor design can be implemented with less design margin. Relaxing design margins will result in smaller, simpler and less expensive sensor systems providing competitive advantage over multi-sensor systems that do not use the techniques described.

The system ensures robust data collection in a dynamic sensing environment by allowing technically naïve users to isolate faults to a specific sensor.

The system relieves sensor devices with modest processing resources of the burden of self-diagnosis.

The system is extensible and supports remote management and customization.

Figure 1:
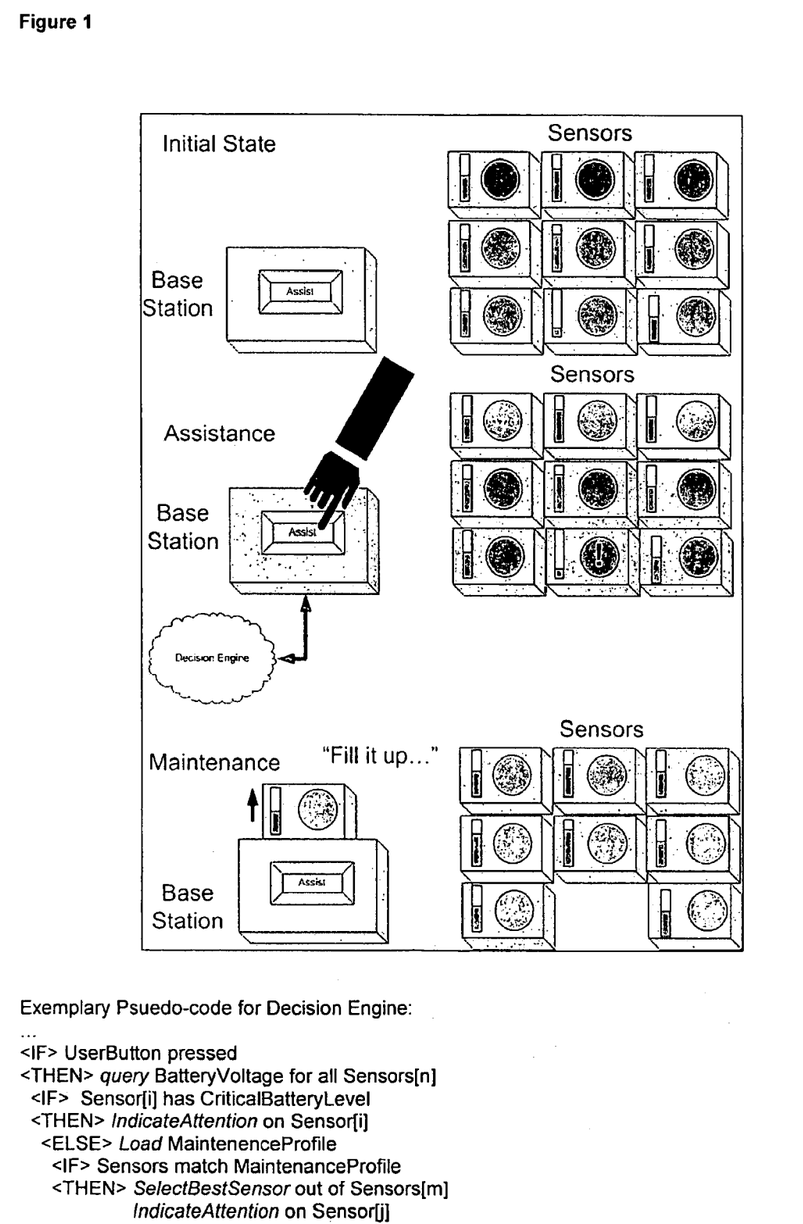
FIG. 1 illustrates an exemplary embodiment in accordance with the present invention.
Figure 2:
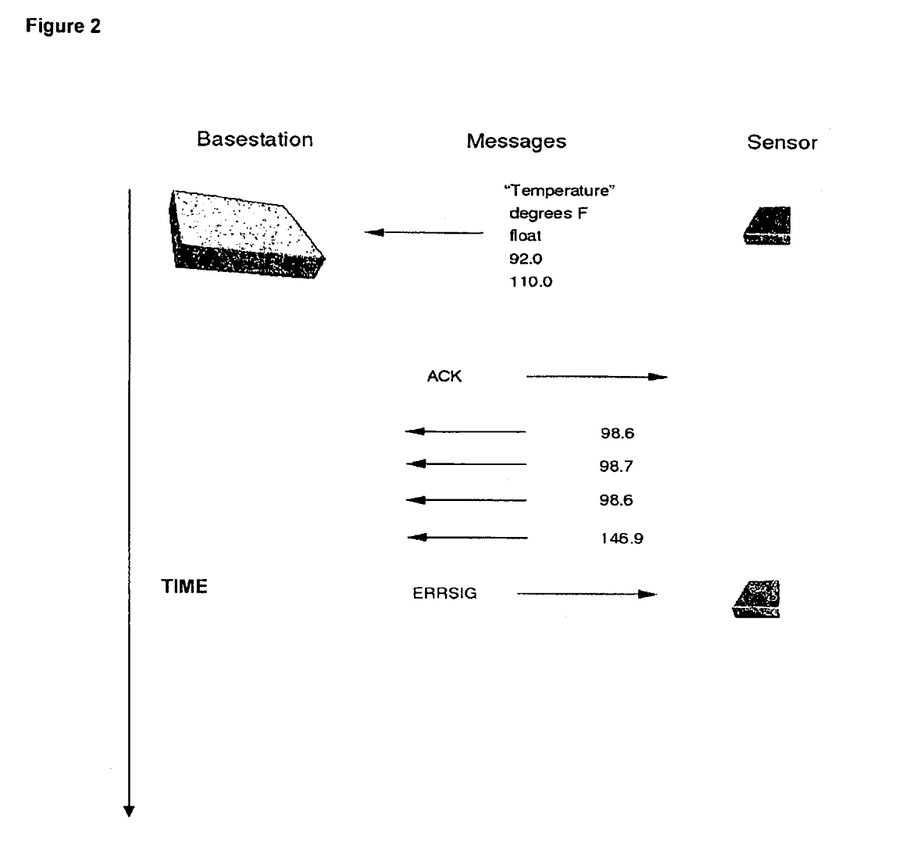
FIG. 2 illustrates an exemplary flow between the base state, messages and sensors in accordance with an embodiment of the invention.
Figure 3:
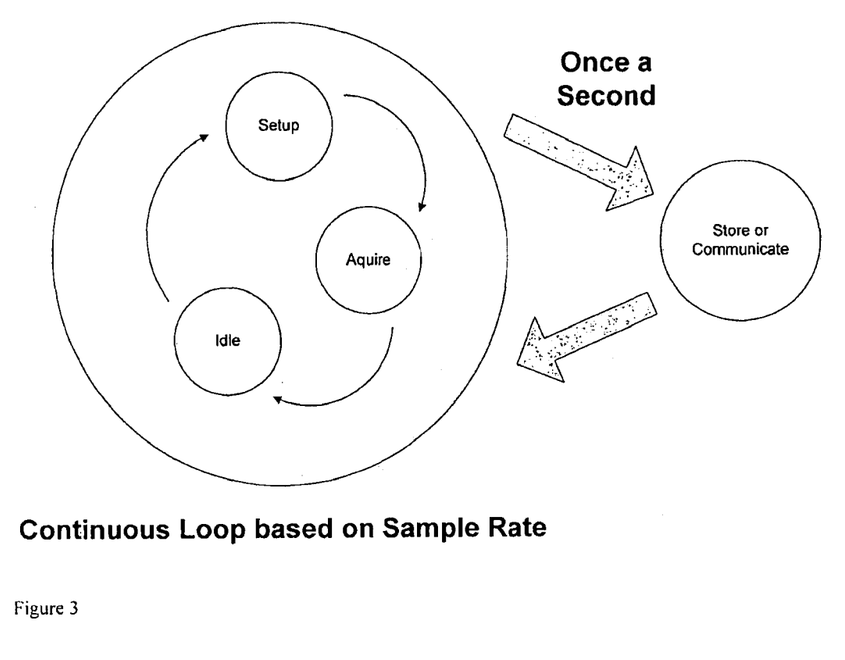
FIG. 3 illustrates an exemplary flow diagram of a continuous loop based on sample rate.
Figure 4:
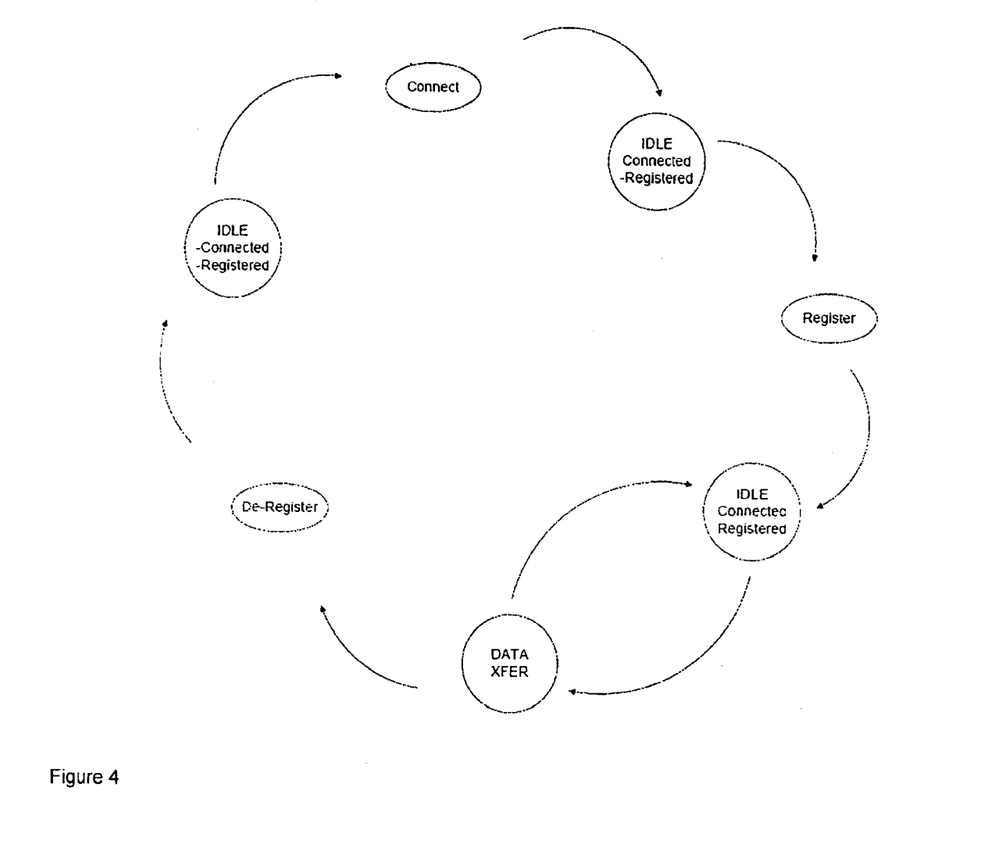
FIG. 4 illustrates an exemplary flow of connection, registration and data transfer for the sensor.

An exemplary embodiment of one detailed application relates to the case of a multi-limb motion capture system for physical rehabilitation, such as stroke recovery. Referring to the embodiment in FIG. 1, ten sensors with 7-day battery life and recording capability are placed on the body (one for each limb segment and two on the torso). Data from accelerometers in the sensor will be used to form a detailed model of body kinetics to guide treatment. The data set created by monitoring the sensors will be especially valuable since the user will be performing natural activities. However, maintaining ten sensors, for example for 2-3 weeks, is burdensome—they are easily confused and without assistance the user will be forced to charge all ten blindly every few nights to ensure battery life. The charging apparatus will be bulky and intimidating.

To assist the user and dramatically improve the usability of the sensor system, the proposed methods are employed using at least the following decision engine rules:

Ensure sensors have safety margin in remaining battery life; and

Indicate best sensor for charging when prompted by user for maintenance assistance.

The patient can now maintain the sensing system, for example, based on a simple set of instructions:
1) Every night when you remove the sensors before sleep, go to the small charging base-station and press the button.
2) Place the sensor with an indicator illuminated in the base-station for maintenance (in this case data transfer and battery charging).

Over, for example, the three week period of monitoring as described above, the sensors are rotated through the base-station and the simple maintenance procedure becomes second nature much like charging a cellular phone.

Figure 5:
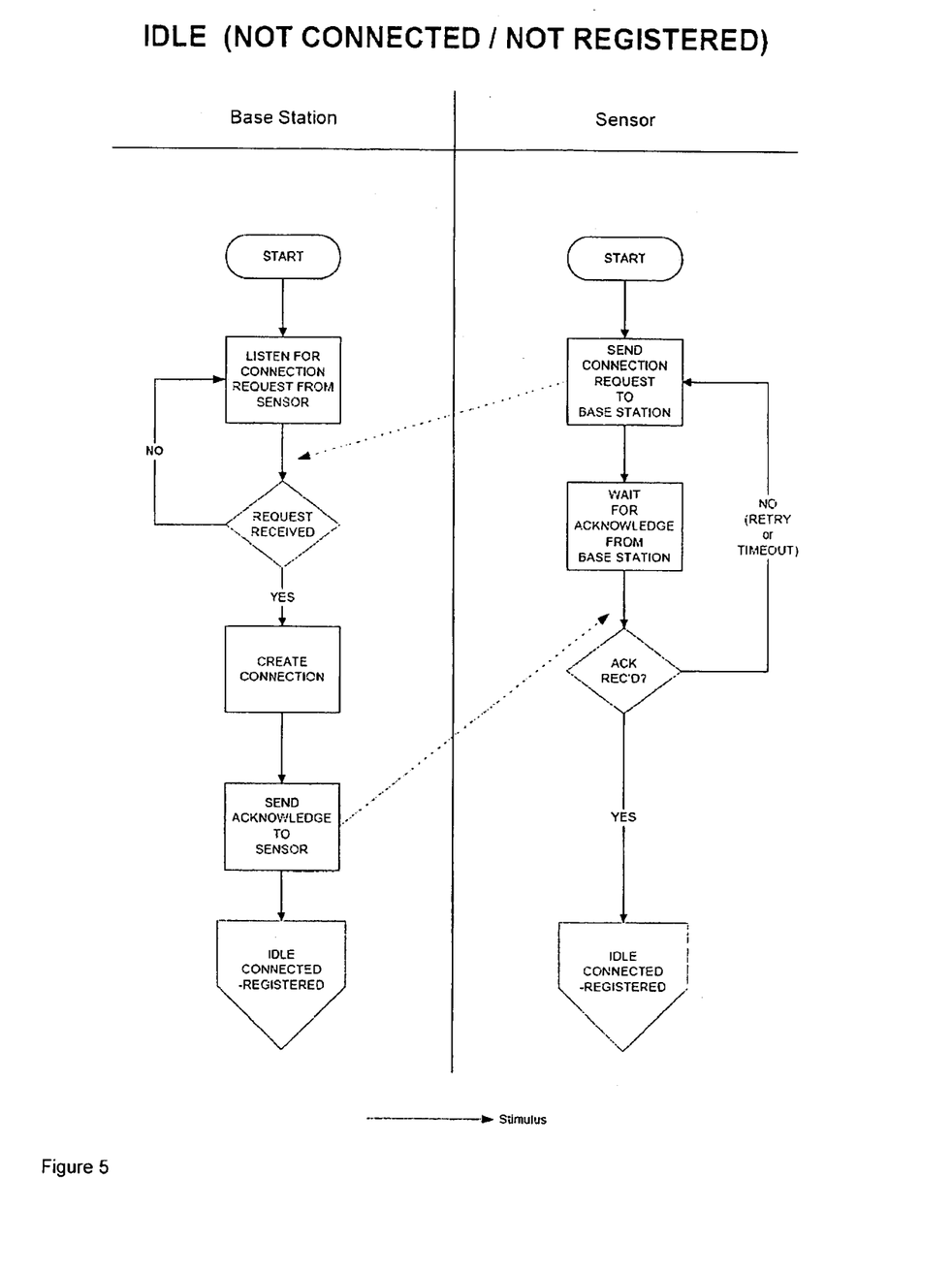
FIG. 5 illustrates an exemplary flow of data between the base station and sensor when neither are connected.

Referring to the embodiment in FIGS. 5+6, the base station acts as server to sensor clients, which perform a two-step registration process during initialization of communications. The client sends header information to the base station including information including data-type for scalar quantity measured by the device, valid range, units for the scalar, frequency of delivery, and a descriptive character string. The base station replies with an acknowledgement message.

The base station calls a fault detection service to check sensor data for proper operation. A simple example would be to perform temporal and scalar bounds-checking for each sensor's data stream with aberrant values measured against the device's recent historical trend. A more complex system may use modeling and machine learning techniques to qualify the sensed data using additional data sources (time of day, season, etc.)

Sensors can be quite different or have subtle failure modes making manual checking tedious for humans, but the process is easily automated using the method herein described.

The fault detection service can be hosted in the base station or on a remote computing resource depending on the processing requirements.

The sensor acts as client to base station server, but listens for spurious messages from server. After registration, sensor minimizes communications to data transmission. Upon receipt of an error signal from base station, the sensor actuates a human-detectable alarm, for example, a low power blinking LED. A one-touch-for-maintenance system may log a sensor fault but wait for a user button-press to signal a fault.

Referring to the tables below, one method of sensor operating life calculation is to use average current during a repeated sampling window according to the following equation:

$$IAvg=(tStore \times IStore)+(tComm \times IComm)+[(tWindow-Store-tComm) \times IAcq)] \quad (1)$$

MEMs accelerometers are useful sensors. The following table was populated based on the operating specifications of an ultra-low power CPU acquiring 16 bit samples for X-Y-Z data using DMA and power saving modes (subject to timing constraints).

| Sampling Rate (Hz), use | IAcq (mA) | Bits per second |
|---|---|---|
| 10, activity segmentation | .090 | 480 |
| 50, gesture recognition | .44 | 2400 |
| 100, clinical grade measurement | .90 | 4800 |

Using conservative values of 20 mA for IStore (better then state-of-the-art for reliable standards based wireless communication or flash media) and an aggressive transfer rate of 0.5 Mbps the following table can be computed using the previous table and equation 1. The table shows best case sensor operating life for 4 common form factors:

| Sampling Rate (Hz) | tStore (s) | IAvg (mA) | Button, 100 mAh | Key-Fob, 250 mAh | Pager, 500 mAh | Phone, 1000 mAh |
|---|---|---|---|---|---|---|
| 10 | .001 | .12 | 35 days | 87 days | 174 days | 350 days |
| 50 | .005 | .30 | 14 days | 35 days | 69 days | 140 days |
| 100 | .01 | .59 | 7 days | 18 days | 35 days | 70 days |

Adding extra degrees of sensing will result in even shorter operating life—e.g. ½ as long when collecting all 6-axis of motion.

Returning to the case of a clinical grade gait and motion capture system using 9 sensors, each sensor would require a 500 mAh battery for one month of data capture. The proposed system for assisted maintenance would allow the user to continuously rotate through considerably smaller sensors without guidance from a caregiver. For example, a key-fob sized device would provide margin and a single sensor could be recharged every night. If the sensor system requires wireless communication, real-world data transfer rates can be up to 100× worse then the numbers above due to packet loss.

Alternatively, in a preferred embodiment with reference to Table 10 and FIG. 7, sensor operation is repetitive and can be expressed as a repetitive loop consisting of states for data acquisition, data storage, data communication, and sensor idle. Over time, the average power consumed by the sensor will be equal to a sum of terms for power in each state weighted by time spent in each state. In the likely worst case, current draw for each state can be determined from a static value from device datasheets.

For battery powered devices, power is approximated by=Current draw on a battery with a manufacturer's mAh rating. Therefore power in a state is approximated by current, not current*voltage.

From these assertions, an equation for average current in a repetitive loop is derived:

Average Current/Many Identical Loops~=Current/Loop

Average Current=[Time spent storing*Current while storing]+[Time spent communicating*Current while communicating]+[Time spent in setup to acquiring data*Current in setup to acquiring data]+[Time spent acquiring data*Current while acquiring data]+[Time spent Idle*Current while Idle]

$$IAvg=[tStore*IStore]+[tComm*IComm]+[tSetup*ISetup]+[tAcq*IAcq]+[tIdle*IIdle] \quad (1)$$

It can be observed that:

$$tLoop=tStore+tComm+tSetup+tAcq+tIdle \quad (2)$$

To simplify notation, an average current for Setup, Acquire and Idle states is calculated as illustrated in 100 Hz Sampling table 10:

The acquisition process uses data from datasheets for timing requirements and current consumption (eg. 1.3 mA=ICPUinDMA+IADC+IAccelerometer) and involves the following states:

1) Idle;
2) Enable on the accelerometer so that power can stabilize (setup to Acquiring data); and
3) Enable the ADC and sample X/Y/Z data points.

The number in the time row is the sample period, the number below is the calculated average current.

Bits per second can be calculated easily:

Samples per second*bits per sample*channels sampled=bits per second.

For 10 Hz:

10*16*3=480 bps

For 50 Hz, the value is 2400 bps
For 100 Hz the value is 4800 bps
From this we get the completed first and second tables above.
So:

$$IAvg=[tStore*IStore]+[0*IComm]+[tSampling*ISampling] \quad (2)$$

See Continuous Loop based on Sample Rate (FIG. 7).

tStore=Bits per second/data transfer rate.

tSampling and ISample are calculated based on the sample rate chart above.

The second table above is based on plugging results to equation (1) using Istore=20 ma and a data transfer rate of 0.5 Mbps. Also tComm is set to zero since Istore is less then IComm in most cases.

For 10 Hz and communication every second:

$I\text{avg}=((0.001\text{ s})*20\text{ mA})+(1\text{ s}-0.001\text{ s})*0.091$
$\text{mA}=0.11\text{ mA}$ For 50 Hz and communication every second:

$I\text{avg}=((0.005\text{ s})*20\text{ mA})+(1\text{ s}-0.005\text{ s})*0.44$
$\text{mA}=0.53\text{ mA}$ For 100 Hz and communication every second:

$I\text{avg}=((0.010\text{ s})*20\text{ mA})+(1\text{ s}-0.010\text{ s})*0.88\text{ mA}=1.1$
$\text{mA}$ Finally, battery life is calculated using the formula:

Operating life (hrs)=[(Battery capacity (mAh)/$I$avg)]

Operating life days=Operating life hrs/24

For 10 Hz:

100 mAh/0.11 ma=909 hrs=38 days 250 mAh/0.11 ma=2272 hrs=95 days 500 mAh/0.11 ma=4545 hrs=189 days 1000 mAh/0.11 ma=9091 hrs=379 days For 50 Hz:

100 mAh=8 days 250 mAh=20 days 500 mAh=39. days 1000 mAh=79 days

For 100 Hz:

100 mAh=4 days 250 mAh=10 days 500 mAh=19 days 1000 mAh=38 days

Most sensors are electrical or electronic, although other types exist. A sensor is a type of transducer. Direct indicating sensors, for example, a mercury thermometer, are human readable. Other sensors must be paired with an indicator or display, for instance a thermocouple.

Sensors are used in everyday life. Applications include automobiles, machines, aerospace, medicine, industry and robotics.

Technical progress allows more and more sensors to be manufactured with MEMS technology. In most cases this offers the potential to reach a much higher sensitivity. See also MEMS sensor generations.

Types

Since a significant change involves an exchange of energy, sensors can be classified according to the type of energy transfer that they detect.

Thermal

Temperature sensors: thermometers, thermocouples, temperature sensitive resistors (thermistors and resistance temperature detectors), bi-metal thermometers and thermostats.

Heat sensors: bolometer, calorimeter.

Electromagnetic

Electrical resistance sensors: ohmmeter, multimeter

Electrical current sensors: galvanometer, ammeter

Electrical voltage sensors: leaf electroscope, voltmeter

Electrical power sensors: watt-hour meters

Magnetism sensors: magnetic compass, fluxgate compass, magnetometer, Hall effect device, Metal detectors Mechanical Pressure sensors: altimeter, barometer, barograph, pressure gauge, air speed indicator, rate of climb indicator, variometer Gas and liquid flow sensors: flow sensor, anemometer, flow meter, gas meter, water meter, mass flow sensor Mechanical sensors: acceleration sensor, position sensor, selsyn, switch, strain gauge Chemical Chemical sensors detect the presence of specific chemicals or classes of chemicals. Examples include oxygen sensors, also known as lambda sensors, ion-selective electrodes, pH glass electrodes, and redox electrodes.

Optical and Radiation

Electromagnetic time-of-flight. Generate an electromagnetic impulse, broadcast it, then measure the time a reflected pulse takes to return. Commonly known as—RADAR (Radio Detection And Ranging) are now accompanied by the analogous LIDAR (Light Detection And Ranging. See following line), all being electromagnetic waves. Acoustic sensors are a special case in that a pressure transducer is used to generate a compression wave in a fluid medium (air or water) light time-of-flight. Used in modern surveying equipment, a short pulse of light is emitted and returned by a retroreflector. The return time of the pulse is proportional to the distance and is related to atmospheric density in a predictable way.

Ionising Radiation

Radiation sensors: Geiger counter, dosimeter, Scintillation counter, Neutron detection.

Subatomic sensors: Particle detector, scintillator, Wire chamber, cloud chamber, bubble chamber. See Category:Particle_detectors Non-Ionising Radiation Light sensors, or photodetectors, including semiconductor devices such as photocells, photodiodes, phototransistors, CCDs, and Image sensors; vacuum tube devices like photo-electric tubes, photomultiplier tubes; and mechanical instruments such as the Nichols radiometer.

Infrared sensor, especially used as occupancy sensor for lighting and environmental controls.

Proximity sensor—A type of distance sensor but less sophisticated. Only detects a specific proximity. May be optical—combination of a photocell and LED or laser. Applications in cell phones, paper detector in photocopiers, auto power standby/shutdown mode in notebooks and other devices. May employ a magnet and a Hall effect device.

Scanning laser—A narrow beam of laser light is scanned over the scene by a mirror. A photocell sensor located at an offset responds when the beam is reflected from an object to the sensor, whence the distance is calculated by triangulation.

Focus. A large aperture lens may be focused by a servo system. The distance to an in-focus scene element may be determined by the lens setting.

Binocular. Two images gathered on a known baseline are brought into coincidence by a system of mirrors and prisms. The adjustment is used to determine distance. Used in some cameras (called range-finder cameras) and on a larger scale in early battleship range-finder Interferometry. Interference fringes between transmitted and reflected lightwaves produced by a coherent source such as a laser are counted and the distance is calculated. Capable of extremely high precision.

Scintillometers measure atmospheric optical disturbances.

Acoustic

Sound sensors: microphones, hydrophones, seismometers.

Acoustic: uses ultrasound time-of-flight echo return. Used in mid 20th century polaroid cameras and applied also to robotics. Even older systems like Fathometers (and fish finders) and other 'Tactical Active' Sonar (Sound Navigation And Ranging) systems in naval applications which mostly use audible sound frequencies.

Other Types

Motion sensors: radar gun, speedometer, tachometer, odometer, occupancy sensor, turn coordinator Orientation sensors: gyroscope, artificial horizon, ring laser gyroscope Distance sensor (noncontacting) Several technologies can be applied to sense distance: magnetostriction Non Initialized Systems Gray code strip or wheel—a number of photodetectors can sense a pattern, creating a binary number. The gray code is a mutated pattern that ensures that only one bit of information changes with each measured step, thus avoiding ambiguities.

Initialized Systems

These require starting from a known distance and accumulate incremental changes in measurements.

Quadrature wheel—An disk-shaped optical mask is driven by a gear train. Two photocells detecting light passing through the mask can determine a partial revolution of the mask and the direction of that rotation.

Whisker sensor—A type of touch sensor and proximity sensor.

Microelectromechanical Systems (MEMS): is the technology of the very small, and merges at the nanoscale into "Nanoelectromechanical" Systems (NEMS) and Nanotechnology. In Europe, MEMS are often referred to as Micro Systems Technology (MST). It should not be confused with the hypothetical vision of Molecular nanotechnology or Molecular Electronics. These devices generally range in size from a micrometer (a millionth of a meter) to a millimeter (thousandth of a meter). At these size scales, a human's intuitive sense of physics does not always hold true. Due to MEMS' large surface area to volume ratio, surface effects such as electrostatics and wetting dominate volume effects such as inertia or thermal mass. They are fabricated using modified silicon fabrication technology (used to make electronics), molding and plating, wet etching (KOH, TMAH) and dry etching (RIE and DRIE), electro discharge machining (EDM), and other technologies capable of manufacturing very small devices. MEMS sometimes go by the names micromechanics, micro machines, or micro system technology (MST).

Common applications include:

Inkjet printers, which use piezoelectrics or bubble ejection to deposit ink on paper.

Accelerometers in modern cars for a large number of purposes including airbag deployment in collisions.

MEMS gyroscopes used in modern cars and other applications to detect yaw; e.g. to deploy a roll over bar or trigger dynamic stability control.

Pressure sensors e.g. car tire pressure sensors, and disposable blood pressure sensors.

Displays e.g the DMD chip in a projector based on DLP technology has on its surface several hundred thousand micromirrors.

Optical switching technology which is used for switching technology for data communications, and is part of the emerging technology of smartdust.

The motion-sensing controller in the Nintendo Wii video game system represents a popular consumer application of MEMS technology.

Finite element analysis is an important part of MEMS design.

Flash memory: is a form of non-volatile computer memory that can be electrically erased and reprogrammed. It is a technology that is primarily used in memory cards. Unlike EEPROM, it is erased and programmed in blocks consisting of multiple locations (in early flash the entire chip had to be erased at once). Flash memory costs far less than EEPROM and therefore has become the dominant technology wherever a significant amount of non-volatile, solid-state storage is needed. Examples of applications include digital audio players, digital cameras and mobile phones. Flash memory is also used in USB flash drives (thumb drives, handy drive), which are used for general storage and transfer of data between computers. It has also gained some popularity in the gaming market, where it is often used instead of EEPROMs or battery-powered SRAM for game save data.

Automation: roboticization or industrial automation or numerical control is the use of control systems such as computers to control industrial machinery and processes, replacing human operators. In the scope of industrialization, it is a step beyond mechanization. Whereas mechanization provided human operators with machinery to assist them with the physical requirements of work, automation greatly reduces the need for human sensory and mental requirements as well.

There are still many jobs which are in no immediate danger of automation. No device has been invented which can match the human eye for accuracy and precision in many tasks; nor the human ear. Even the admittedly handicapped human is able to identify and distinguish among far more scents than any automated device. Human pattern recognition, language recognition, and language production ability is well beyond anything currently envisioned by automation engineers.

Specialized hardened computers, referred to as programmable logic controllers (PLCs), are frequently used to synchronize the flow of inputs from (physical) sensors and events with the flow of outputs to actuators and events. This leads to precisely controlled actions that permit a tight control of almost any industrial process. (It was these devices that were feared to be vulnerable to the "Y2K bug", with such potentially dire consequences, since they are now so ubiquitous throughout the industrial world.)

The process of circuit design can cover systems ranging from national power grids all the way down to the individual transistors within an integrated circuit. For simple circuits the design process can often be done by one person without needing a planed or structured design process, but for more complex designs, teams of designers following a systematic approach with intelligently guided computer simulation are becoming increasingly common.

Formal circuit design usually involves the following stages:

Sometimes, writing the requirement specification after liaising with the customer Writing a technical proposal to meet the requirements of the customer specification Synthesising on paper an abstract electrical or electronic circuit that will meet the specifications Calculating the component values to meet the operating specifications under specified conditions Building a breadboard or other prototype version of the design and testing against specification Making any alterations to the circuit to achieve compliance Choosing a method of construction as well as all the parts and materials to be used Presenting component and layout information to draughtspersons, and layout and mechanical engineers, for prototype production Testing or type-testing a number of prototypes to ensure compliance with customer requirements Signing and approving the final manufacturing drawings Post-design services (obsolescence of components etc.)

Specification

The process of circuit design begins with the specification, which states the functionality that the finished design must provide, but does not indicate how it is to be achieved. The initial specification is basically a technically detailed description of what the customer wants the finished circuit to achieve and can include a variety of electrical requirements, such as what signals the circuit will receive, what signals it must output, what power supplies are available and how much power it is permitted to consume. The specification can (and normally does) also set some of the physical parameters that the design must meet, such as size, weight, moisture resistance, temperature range, thermal output, vibration tolerance and acceleration tolerance.

As the design process progresses the designer(s) will frequently return to the specification and alter it to take account of the progress of the design. This can involve tightening specifications that the customer has supplied, and adding tests that the circuit must pass in order to be accepted. These additional specifications will often be used in the verification of a design. Changes that conflict with or modify the customer's original specifications will almost always have to be approved by the customer before they can be acted upon.

Correctly identifying the customer needs can avoid a condition known as 'design creep' which occurs in the absence of realistic initial expectations, and later by failing to communicate fully with the client during the design process. It can be defined in terms of its results; "at one extreme is a circuit with more functionality than necessary, and at the other is a circuit having an incorrect functionality". (DeMers, 1997) Nevertheless some changes can be expected and it is good practice to keep options open for as long as possible because it's easier to remove spare elements from the circuit later on than it is to put them in.

Design

The design process involves moving from the specification at the start, to a plan that contains all the information needed to be physically constructed at the end, this normally happens by passing through a number of stages, although in very simple circuit it may be done in a single step. The process normally begins with the conversion of the specification into a block diagram of the various functions that the circuit must perform, at this stage the contents of each block are not considered, only what each block must do, this is sometimes referred to as a "black box" design. This approach allows the possibly very complicated task to be broken into smaller tasks which may either by tackled in sequence or divided amongst members of a design team.

Each block is then considered in more detail, still at an abstract stage, but with a lot more focus on the details of the electrical functions to be provided. At this or later stages it is common to require a large amount of research or mathematical modeling into what is and is not feasible to achieve. The results of this research may be fed back into earlier stages of the design process, for example if it turns out one of the blocks cannot be designed within the parameters set for it, it may be necessary to alter other blocks instead. At this point it is also common to start considering both how to demonstrate that the design does meet the specifications, and how it is to be tested (which can include self diagnostic tools).

Finally the individual circuit components are chosen to carry out each function in the overall design, at this stage the physical layout and electrical connections of each component are also decided, this layout commonly taking the form of artwork for the production of a printed circuit board or Integrated circuit. This stage is typically extremely time consuming because of the vast array of choices available. A practical constraint on the design at this stage is that of standardization, while a certain value of component may be calculated for use in some location in a circuit, if that value cannot be purchased from a supplier, then the problem has still not been solved. To avoid this a certain amount of 'catalog engineering' can be applied to solve the more mundane tasks within an overall design.

Costs

Proper design philosophy incorporates economic and technical considerations and keeps them in balance at all times, and right from the start. Balance is the key concept here; just as many delays and pitfalls can come from ill considered cost cutting as with cost overruns. Good accounting tools (and a design culture that fosters their use) is imperative for a successful project. "Manufacturing costs shrink as design costs soar," is oft quoted as a truism in circuit design, particularly for IC's.

Verification and Testing

Once a circuit has been designed, it must be both verified and tested. Verification is the process of going through each stage of a design and ensuring that it will do what the specification requires it to do. This is frequently a highly mathematical process and can involve large-scale computer simulations of the design. In any complicated design it is very likely that problems will be found at this stage and may involve a large amount of the design work be redone in order to fix them Testing is the real-world counterpart to verification, testing involves physically building at least a prototype of the design and then (in combination with the test procedures in the specification or added to it) checking the circuit really does do what it was designed to.

Prototyping

Prototyping is a means of exploring ideas before an investment is made in them. Depending on the scope of the prototype and the level of detail required, prototypes can be built at any time during the project. Sometimes they are created early in the project, during the planning and specification phase, commonly using a process known as breadboarding; that's when the need for exploration is greatest, and when the time investment needed is most viable. Later in the cycle packaging mock-ups are used to explore appearance and usability, and occasionally a circuit will need to be modified to take these factors into account.

Results

As circuit design is the process of working out the physical form that an electronic circuit will take, the result of the circuit design process is the instructions on how to construct the physical electronic circuit. This will normally take the form of blueprints describing the size, shape, connectors, etc in use, and artwork or CAM file for manufacturing a printed circuit board or Integrated circuit.

Documentation

Any commercial design will normally also include an element of documentation, the precise nature of this documentation will vary according to the size and complexity of the circuit as well as the country in which it is to be used. As a bare minimum the documentation will normally include at least the specification and testing procedures for the design and a statement of compliance with current regulations. In the EU this last item will normally take the form of a CE Declaration listing the European directives complied with and naming an individual responsible for compliance.

The invention claimed is:

1. A system for maintaining a sensor, comprising:
 a sensor capable of being attached to a user's body and comprising:
  a transceiver configured to transmit data, and
  a sensor attention indicator configured to generate a visual output or an audio output in response to receiving a sensor attention indicator activation command; and
 a base station adapted to receive the data from the sensor, the base station comprising:
  a fault-detection system adapted to detect a faulty operating state of the sensor, and
  a decision engine coupled to the base station and adapted to transmit the sensor attention indicator activation command to the sensor based on an indication of the faulty operating state from the fault-detection system.

2. The system of claim 1, wherein the transceiver is a wireless transceiver adapted to wirelessly transmit data, and wherein the base station is adapted to wirelessly receive the data from the sensor.

3. The system of claim 1, wherein the fault-detection system is adapted to detect the faulty operating state based on the data received from the sensor.

4. The system of claim 1, wherein the corresponding sensor is a MEMS accelerometer.

5. The system of claim 1, wherein the base station is adapted to start a registration process with the sensor by receiving information about the sensor.

6. The system of claim 5, wherein the information about the sensor includes information about a valid data type for data measured by the sensor, a valid range for data measured by the sensor, a valid unit for data measured by the sensor, or a frequency of delivery for data measured by the sensor.

7. The system of claim 1, wherein the decision engine is adapted to receive user profile data from a health care provider.

8. The system of claim 1, wherein the decision engine is adapted to receive information indicative of battery life of the sensor and to determine whether the battery life of the sensor is within a safety margin.

9. The system of claim 1, wherein the base station is adapted to communicate the sensor data to a health monitoring system.

10. The system of claim 1, wherein the base station further comprises a user input device adapted to receive a user request related to maintenance of the sensor, and wherein the decision engine is configured to transmit the sensor attention indicator activation command in response to receiving the request from the user input device.

11. The system of claim 10, wherein the user input device comprises a button.

12. The system of claim 1, wherein the base station further comprises a housing adapted to receive the sensor and to provide battery charging power to the sensor, and wherein the fault-detection system is configured to detect the faulty operating state of the sensor by determining a remaining battery life of the sensor.

13. A method for maintaining a sensor, comprising:
 receiving wirelessly, at a base station, data from a sensor;
 detecting, at the base station, a faulty operating state of the sensor based on sensor data received from the sensor; and
 transmitting wirelessly a sensor attention indicator activation command to the sensor
based on an indication of the faulty operating state of the sensor.

14. An apparatus for maintaining a sensor, comprising:
 a transceiver adapted to receive data from a sensor;
 a fault-detection system adapted to detect a faulty operating state of the sensor based on sensor data received from the sensor; and
 a decision engine adapted to transmit a sensor attention indicator activation command
 to the sensor based on an indication of the faulty operating state of the sensor from the fault-detection system.

* * * * *

UNITED STATES PATENT AND TRADEMARK OFFICE
CERTIFICATE OF CORRECTION

PATENT NO. : 8,441,371 B2
APPLICATION NO. : 13/618584
DATED : May 14, 2013
INVENTOR(S) : Benjamin Kuris et al.

Page 1 of 1

It is certified that error appears in the above-identified patent and that said Letters Patent is hereby corrected as shown below:

On title page, item (75) Inventors, Line 2
     replace "Shirley, AA"
     with --Shirley, MA--.

Signed and Sealed this
Twenty-fifth Day of June, 2013

Teresa Stanek Rea
*Acting Director of the United States Patent and Trademark Office*